United States Patent [19]
McKinney et al.

[11] Patent Number: 5,433,994
[45] Date of Patent: Jul. 18, 1995

[54] SUPERABSORBENT STRUCTURE

[76] Inventors: Betty J. McKinney, 2610 Columbus Cir., Charlotte, N.C. 28208; Joanne C. Maheras, 1800 Summerhill Dr., Charlotte, N.C. 28212; Ronald J. Foltz, 19909 Stough Farm Rd., Huntersville, N.C. 28078; Steven F. Nielsen, 653 Coulwood Drive, Charlotte, N.C. 28214; Ronald O. Bryant, 1100 Ardsley Rd., Charlotte, N.C. 28207; John B. Hopkins, P.O. Box 1004, Pineville, N.C. 28134

[21] Appl. No.: 994,210

[22] Filed: Dec. 18, 1992

[51] Int. Cl.$^6$ ............................................. B32B 7/00
[52] U.S. Cl. ............................... 428/246; 428/284; 428/286; 428/304.4; 428/314.4; 428/343; 428/354
[58] Field of Search ............... 428/283, 284, 913, 246, 428/286, 304.4, 314.4, 343, 354

[56] References Cited

U.S. PATENT DOCUMENTS

| | | | |
|---|---|---|---|
| 3,669,103 | 6/1972 | Harper et al. | 128/156 |
| 4,069,366 | 1/1978 | Hoey | 428/310 |
| 4,076,663 | 2/1978 | Masuda et al. | 260/17.4 |
| 4,115,332 | 9/1978 | Young et al. | 260/17.4 |
| 4,133,784 | 1/1979 | Otey et al. | 260/17.4 |
| 4,197,371 | 4/1980 | Holst et al. | 521/84 |
| 4,200,558 | 4/1980 | Holst et al. | 260/17 A |
| 4,337,181 | 6/1982 | Otey et al. | 523/128 |
| 4,454,268 | 6/1984 | Otey et al. | 524/47 |
| 4,560,372 | 12/1985 | Pieniak | 604/369 |
| 4,676,784 | 6/1987 | Erdman et al. | 604/368 |

FOREIGN PATENT DOCUMENTS

| | | |
|---|---|---|
| 0278601 | 1/1988 | European Pat. Off. . |
| 0425269 | 10/1990 | European Pat. Off. . |
| 0425270 | 10/1990 | European Pat. Off. . |
| 57-92032 | 6/1982 | Japan . |
| 1034296 | 6/1966 | United Kingdom . |
| 2203985 | 11/1988 | United Kingdom . |
| WO91/04361 | 4/1991 | WIPO . |

OTHER PUBLICATIONS

Advertisement by Pacific, dated 1987.
Advertisement by Prince Mfg. Inc., dated 1992.

*Primary Examiner*—James J. Bell
*Attorney, Agent, or Firm*—R. H. Hammer, III

[57] ABSTRACT

The instant invention is directed to an article of manufacture for absorbing liquids. This invention comprises: a superabsorbent structure; and a permeable means for coating the superabsorbent structure. The superabsorbent structure comprises a superabsorbent polymer mixed into a matrix material, the matrix material being selected from the group consisting of cellulose ester, acrylic acid ester, polyvinyl ester, copolymers of the foregoing and combinations thereof. The permeable means is laminated onto the superabsorbent structure.

11 Claims, 1 Drawing Sheet

SUPERABSORBENT STRUCTURE

FIELD OF THE INVENTION

This invention is directed to a superabsorbent structure.

BACKGROUND OF THE INVENTION

Absorbent structures are known. For example, a product offered by PACIFIC under the tradename "CAPILLAR-SYSTEM" is directed to a tape-like multilayered structure which is highly absorbent to perspiration due to its use of a plurality of mircochannels. Additionally, Prince Manufacturing Inc. of Princeton, N.J. offers several commercial absorbent structures under the tradenames "VORTEX", "EXTRA TAC", and "SUPER DRY". All the above noted products are targeted for use as grip surfacing for tennis rackets.

SUMMARY OF THE INVENTION

The instant invention is directed to an article of manufacture for absorbing liquids. This invention comprises: a superabsorbent structure; and a permeable means for coating the superabsorbent structure. The superabsorbent structure comprises a superabsorbent polymer mixed into a matrix material, the matrix material being selected from the group consisting of cellulose ester, acrylic acid ester, polyvinyl ester, copolymers of the foregoing and combinations thereof. The permeable means is laminated onto the superabsorbent structure.

The object of this invention is to provide an article of manufacture for absorbing liquids which has an enhanced capability for absorbing liquid due to the incorporation of superabsorbent polymers.

DESCRIPTION OF THE DRAWINGS

For the purpose of illustrating the invention, there is shown in the drawings a form which is presently preferred; it being understood, however, that this invention is not limited to the precise arrangement and instrumentality shown.

DETAILED DESCRIPTION OF THE INVENTION

Figure 1:
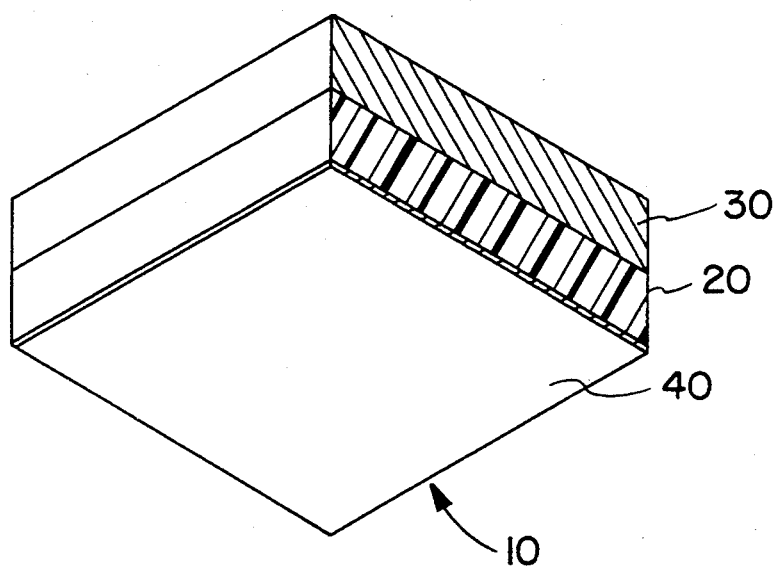
FIG. 1 is an isometric view of a portion of the superabsorbent structure made according to the present invention.

Referring to the drawings, wherein like numerals indicate like elements, there is shown in FIG. 1 an embodiment of the instant invention, liquid absorbing device 10. Device 10 comprises a superabsorbent structure 20, and a permeable means 30. Superabsorbent structure 20 and permeable mean 30 are joined together in a conventional manner so that liquid may pass through permeable means 30 to absorbent structure 20. Optionally, an adhesive means 40 maybe applied to the side of superabsorbent structure 20 opposite the permeable mean 30. The specifics of superabsorbent structure 20, permeable means 30 and adhesive means 40 shall be discussed in greater detail below.

Figure 2:
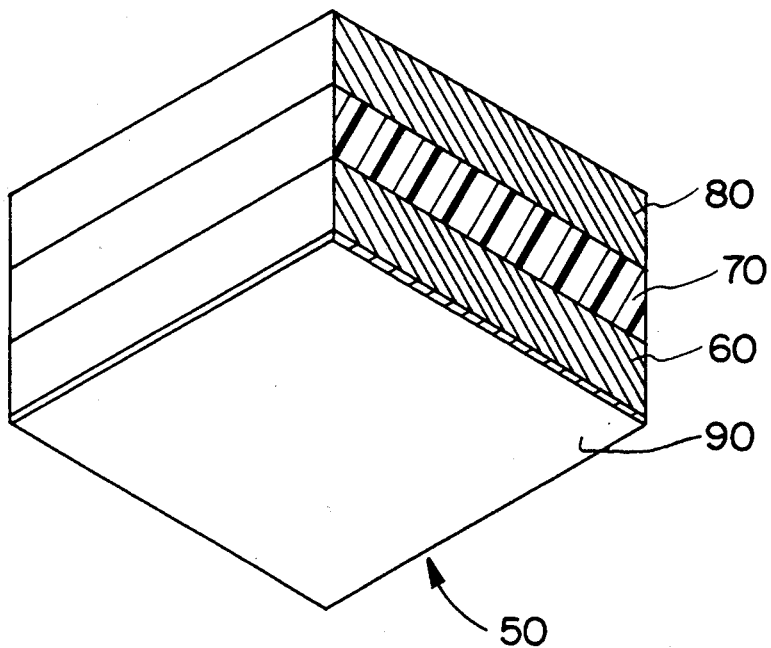
FIG. 2 is an isometric view of an alternate embodiment of the superabsorbent structure made according to the present invention.

Referring to FIG. 2, an alternate embodiment of the instant invention, liquid absorbing device 50, is shown. Device 50 comprises a superabsorbent structure 70, a permeable means 80, a cushioning means 60, and, optionally, an adhesive means 90. Superabsorbent structure 70 is sandwiched between permeable means 80 and cushioning means 60. Permeable means 80 and superabsorbent structure 70 are joined together in any known manner so as not to impede the free flow of liquid through permeable means 80. Superabsorbent structure 70 and cushioning means 60 are joined together, however, the passage of liquid from structure 70 to cushioning means 60 is less important. Optionally, an adhesive means 90 maybe placed on the side of the cushioning means 60 opposite the superabsorbent structure 70.

Embodiments 10 and 50 of the instant invention maybe provided in several forms. Those forms include: sheets, rolled goods, tapes, tubes (in which the permeable means is on the outermost radial surface of the tube), and the like.

Specifics regarding the construction of the superabsorbent structure, 20, 70, the permeable means 30, 80, the cushioning means 60 and the adhesive means 40, 90 are discussed hereinbelow.

Superabsorbent structure 20, 70 comprises a superabsorbent polymer mixed into a matrix material, the matrix material being selected from the group consisting of cellulose esters, acrylic acid esters, polyvinyl esters, copolymers of the foregoing and combinations thereof. This material is disclosed in U.S. patent application Ser. No. 07/805,538 filed Dec. 11, 1991 entitled "Method for Immobilizing Superabsorbent Polymer and Products Derived Therefrom" by Ehrhardt et al which is incorporated herein by reference. The material comprising the superabsorbent structure can be formed into films, sheets, fibers, fibrils, felts of a plurality of fibers, webs of fibers, and various variations thereof, such as laminates. While it is contemplated that superabsorbent structure 20, 90 would be formed into a film or a sheet, it is also possible that it could be in the form of either a woven or nonwoven fabric comprising fiber of the superabsorbent material. The preferred matrix materials of the present invention, when cast or extruded, harden into a non-expanded solid. By non-expanded solid is meant a compressed, or substantially continuous, hardened material. Thus, a non-expanded solid is a material that does not exhibit a visually discernable expanded structural network, e.g. the cellular structure of a foam. By a hardened, solid material is meant that it is not fluid. Despite being characterized as a hardened solid, these materials can be made to be very pliable and flexible. Similarly, the materials can be made to be porous as would be desirable for filtration membranes.

The superabsorbent polymers suitable for application in the present invention are conventional superabsorbent polymers as that term is commonly applied in the art. Examples of such materials are polymers of water soluble acrylic or vinyl monomers that are cross-linked with a polyfunctional reactant. Also included are starch modified polyacrylic acids and hydrolyzed polyacrylonitrile and their alkali metal salts. A more thorough recitation of superabsorbent polymers is presented in U.S. Pat. No. 4,990,541, which is incorporated herein by reference.

A number of such superabsorbent polymers are commercially available and these are also suitable for use in the present invention. A preferred commercially available superabsorbent polymer is Sanwet ® a starch modified superabsorbent polymer available from Hoechst Celanese Corporation, Charlotte, N.C. Sanwet ® is a starch grafted polyacrylate sodium salt that has the capacity to absorb as much as 800 times its own weight in liquid. Other commercially available superabsorbent polymers are: DRYTECH ® 520 SUPERABSORBENT POLYMER available from Dow Chemical Co., Midland, Mich. (Drytech ® is a superabsorbent derived from polypropenoic acid.); AQUA KEEP manufactured by Seitetsu Kagaku Co., Ltd.; ARASORB manufactured by Arakawa Chemical (USA) Inc.,; ARIDALL 1125 manufactured by Chemdall Corporation; and FAVOR manufactured by Stockhausen, Inc.

Examples of suitable matrix materials include: 1) cellulose esters and mixed esters (e.g., cellulose acetate [which term includes cellulose diacetate and cellulose triacetate], cellulose propionate, cellulose butyrate, and mixed esters thereof); 2) polymers of acrylic acid esters (e.g. polymethyl methacrylate and polyethyl methacrylate); and 3) polyvinyl esters (e.g. polyvinyl acetate). Suitable matrix materials further comprise copolymers and combinations thereof. Preferably, the matrix material is cellulose acetate.

The matrix material may further comprise additives to enhance the physicochemical characteristics of the composition and the resulting product. Such additives include conventional plasticizers known to those skilled in the art. Examples of such plasticizers are phthalate esters (e.g., diethyl phthalate and dimethyl phthalate), phosphate esters, low molecular weight polymers (e.g., polypropylene glycol), oleates, sebacates, adipates, fatty acid esters, hydrocarbon derivatives, sulfonamides, and glycol derivatives (e.g., glycerin and modified glycerin such as triacetin).

Permeable mean 30, 80 provides the dual function of allowing liquid to pass therethrough to superabsorbent structure 20, 70 and preventing direct contact of the liquid generating body and the superabsorbent structure. The latter is important because in applications where the liquid generating body is a perspiration generating appendage, for example a hand or a foot, the superabsorbent structure has a "slimy feel". This slimy feel has a detrimental effect on one's ability to firmly grip. Permeable means 30, 80 can be made of numerous materials including, but not limited to open cell foams, paper, woven materials, nonwoven material and permeable membranes. The important considerations in selection of the material for use as the permeable means is its ability to allow moisture to quickly be carried to the superabsorbent structure 20, 70.

Cushioning means 60 is provided to cushion the device when it is used in the form of a grip and thereby improve the "feeling" of the grip made from the embodiment of the instant invention. Additionally, cushioning means 60 may act as a reservoir for excess liquid which may pass through the superabsorbent structure. Cushioning means 60 maybe made of any material including, but is not limited to, open cell foams, closed cell foams, corrugated paperboards, woven materials, and nonwoven materials.

Adhesive means 40, 90 maybe any conventional material as is well known in the art.

The permeable means 30, 80, superabsorbent structure 20, 70 and cushioning means 60 may be joined or laminated in any known manner as set forth above. Explemary methods include, but are not limited to, heat sealing, heat bonding, solution laminating (e.g. with acetone or methyl chloride), adhesive bonding, laminating via perforations, pressure bonding with adhesives, vacuum bonding with adhesives, and the like.

The superabsorbent structures disclosed herein can be used in a variety of applications including, but not limited to, sports equipment handles or grips surfacing, tools handles or grip surfacings, steering wheel covers, gloves, and liners for footwear, sweatband, headgear, dissecants for guncases and cases for musical instruments, seat covers for motorcycles, lawnmowers, bicycles and the like, wound/patch dressing, table cloths, training pads for animals, and medical equipment cleanup pads.

The present invention maybe embodied in other specific forms without departing from the spirit or central attributes thereof and accordingly, reference should be made to the amended claims, rather than to the foregoing specification, as indicated the scope of the invention.

We claim:

1. An article of manufacture for absorbing liquids comprising:
   a superabsorbent structure including a superabsorbent polymer mixed into a nonexpanded solid matrix material, the matrix material being selected from the group consisting of cellulose esters, acrylic acid esters, polyvinyl ester, copolymers of the foregoing and combinations thereof; and
   permeable means overlaying said superabsorbent structure, said permeable means being laminated onto said superabsorbent structure.

2. The article of manufacture according to claim 1 further comprising means for cushioning said superabsorbent structure, said cushioning means being laminated onto said superabsorbent structure.

3. The article according to claim 1 or 2 wherein said matrix material is a cellulose ester.

4. The article according to claim 1 or 2 wherein said matrix material is cellulose acetate.

5. The article according to claim 1 or 2 wherein said matrix material being comprised of a film.

6. The article according to claim 1 or 2 wherein said superabsorbent structure being comprised of a plurality of fibers.

7. The article according to claim 1 or 2 wherein said superabsorbent structure being comprised of a plurality of fibers, said fibers being formed into a felt.

8. The article according to claim 1 or 2 wherein said superabsorbent structure being comprised of a web of fibers.

9. The article according to claim 1 or 2 wherein said superabsorbent structure being comprised of a plurality of fibrels.

10. The article according to claim 1 or 2 wherein said permeable means comprises a material selected from the group of open celled foam, paper, woven materials, nonwoven materials, membranes.

11. The article according to claim 2 wherein said cushioning means comprises a material selected from the group consisting of: open celled foams, closed cell forms, corrugated paperboard, woven material, nonwoven material.

* * * * *